US008012899B2

(12) United States Patent
Hommeltoft

(10) Patent No.: US 8,012,899 B2
(45) Date of Patent: Sep. 6, 2011

(54) RECYCLING OF IONIC LIQUID CATALYST

(75) Inventor: Sven Ivar Hommeltoft, Pleasant Hill, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 434 days.

(21) Appl. No.: 12/343,006

(22) Filed: Dec. 23, 2008

(65) Prior Publication Data

US 2010/0160145 A1    Jun. 24, 2010

(51) Int. Cl.
*B01J 38/68* (2006.01)

(52) U.S. Cl. ............... 502/24; 502/20; 502/21; 502/26; 502/28; 502/35

(58) Field of Classification Search .................. None
See application file for complete search history.

(56) References Cited

U.S. PATENT DOCUMENTS

| | | | |
|---|---|---|---|
| 4,122,245 | A | 10/1978 | Nardi et al. |
| 4,463,071 | A | 7/1984 | Gifford et al. |
| 4,463,072 | A | 7/1984 | Gifford et al. |
| 5,104,840 | A | 4/1992 | Chauvin et al. |
| 5,731,101 | A | 3/1998 | Sherif et al. |
| 6,096,680 | A | 8/2000 | Park |
| 6,797,853 | B2 | 9/2004 | Houzvicka et al. |
| 7,732,364 | B2 * | 6/2010 | Chang et al. ............ 502/53 |
| 2003/0060359 | A1 | 3/2003 | Olivier-Bourbigou et al. |
| 2004/0077914 | A1 | 4/2004 | Zavilla et al. |
| 2004/0133056 | A1 | 7/2004 | Liu et al. |
| 2007/0142211 | A1 | 6/2007 | Elomari et al. |
| 2007/0142213 | A1 | 6/2007 | Elomari et al. |
| 2007/0142217 | A1 | 6/2007 | Elomari et al. |
| 2007/0249485 | A1 | 10/2007 | Elomari et al. |
| 2009/0170687 | A1 | 7/2009 | Luo et al. |
| 2009/0170688 | A1 | 7/2009 | Chang et al. |

OTHER PUBLICATIONS

Miron, et al., "Molecular Structure of Conjunct Polymers", Journal of Chemical and Engineering Data, pp. 150-160 (1963).
Pines, Herman, Saga of a discovery: Alkylation:, Chem Tech, pp. 150-154 (1982).
PCT/US2009/068791 Search Report and Written Opinion, International Filing Date Dec. 18, 2009, 8 pages.

* cited by examiner

*Primary Examiner* — Melvin C Mayes
*Assistant Examiner* — Smita Patel
(74) *Attorney, Agent, or Firm* — Merchant & Gould

(57) ABSTRACT

Provided is a process for safely transporting or recycling an ionic liquid catalyst based on chloroaluminates. The process comprises mixing a secondary alcohol with an ionic liquid based on a chloroaluminate and allowing a reaction to occur forming an aluminum chloride adduct precipitate. The precipitate is filtered and the secondary alcohol removed, leaving a solid salt. This solid salt is the ionic liquid catalyst absent aluminum chloride, for example, Nbutylpyridinium chloride. This salt is recycled to the reactor. $AlCl_3$ is added to the salt prior to introduction into the reactor to remake the ionic liquid catalyst, for example, Nbutylpyridinium heptachloroaluminate.

26 Claims, No Drawings

RECYCLING OF IONIC LIQUID CATALYST

FIELD OF ART

The present disclosure relates to the recycling of regenerated ionic liquid catalysts. More particularly, the present disclosure relates to recycling the halide salt of the ionic liquid catalyst.

BACKGROUND

Ionic liquids are liquids that are composed entirely of ions. The so-called "low temperature" ionic liquids are generally organic salts with melting points under 100 degrees C., or often even lower than room temperature. Ionic liquids may be suitable, for example, for use as a catalyst and as a solvent in alkylation. One class of ionic liquids is fused salt compositions, which are molten at low temperature and are useful as catalysts, solvents, and electrolytes. Such compositions are mixtures of components which are liquid at temperatures below the individual melting points of the components.

Ionic liquids can be defined as liquids whose make-up is entirely comprised of ions as a combination of cations and anions. The most common ionic liquids are those prepared from organic-based cations and inorganic or organic anions. The most common organic cations are ammonium cations, but phosphonium and sulphonium cations are also frequently used. Ionic liquids of pyridinium and imidazolium are perhaps the most commonly used cations. Anions include, but are not limited to, $BF_4{-}$, $PF_6{-}$, haloaluminates such as $Al_2Cl_7{-}$ and $Al_2Br_7{-}$, $[(CF_3SO_2)_2N]{-}$, alkyl sulphates ($RSO_3{-}$), carboxylates ($RCO_2{-}$) and many others. The most catalytically interesting ionic liquids are those derived from ammonium halides and Lewis acids (such as $AlCl_3$, $TiCl_4$, $SnCl_4$, $FeCl_3$ . . . etc.). Chloroaluminate ionic liquids are perhaps the most commonly used ionic liquid catalyst systems.

Examples of such low temperature ionic liquids or molten fused salts are the chloroaluminate salts. Alkyl imidazolium or pyridinium salts, for example, can be mixed with aluminum trichloride ($AlCl_3$) to form the fused chloroaluminate salts. The use of the fused salts of 1-alkylpyridinium chloride and aluminum trichloride as electrolytes is discussed in U.S. Pat. No. 4,122,245. Other patents which discuss the use of fused salts from aluminum trichloride and alkylimidazolium halides as electrolytes are U.S. Pat. Nos. 4,463,071 and 4,463,072. U.S. Pat. No. 5,104,840 describes ionic liquids which comprise at least one alkylaluminum dihalide and at least one quaternary ammonium halide and/or at least one quaternary ammonium phosphonium halide; and their uses as solvents in catalytic reactions.

U.S. Pat. No. 6,096,680 describes liquid clathrate compositions useful as reusable aluminum catalysts in Friedel-Crafts reactions. In one embodiment, the liquid clathrate composition is formed from constituents comprising (i) at least one aluminum trihalide, (ii) at least one salt selected from alkali metal halide, alkaline earth metal halide, alkali metal pseudohalide, quaternary ammonium salt, quaternary phosphonium salt, or ternary sulfonium salt, or a mixture of any two or more of the foregoing, and (iii) at least one aromatic hydrocarbon compound. Aluminum-containing catalysts are among the most common Lewis acid catalysts employed in Friedel-Crafts reactions. Friedel-Crafts reactions are reactions which fall within the broader category of electrophilic substitution reactions including alkylations.

Other examples of ionic liquids and their methods of preparation may also be found in U.S. Pat. Nos. 5,731,101; 6,797,853 and in U.S. Patent Application Publications 2004/0077914 and 2004/0133056.

As a result of use, ionic liquid catalysts become deactivated, i.e. lose activity, and may eventually need to be replaced. Alkylation processes utilizing an ionic liquid catalyst form by-products known as conjunct polymers. These conjunct polymers deactivate the ionic liquid catalyst by forming complexes with the ionic liquid catalyst. Conjunct polymers are highly unsaturated molecules. As the conjunct polymer concentration increases, the activity of the ionic liquid catalysts becomes impaired or at least compromised. Conjunct polymers may also become chlorinated and through their chloro groups may interact with aluminum trichloride and therefore reduce the overall activity of the catalyst or lessen its effectiveness as a catalyst for the intended purpose such as alkylation. Deactivation of the ionic liquid catalyst by conjunct polymers is not only problematic for the alkylation chemistry, but also weighs in heavily on the economics of using ionic liquids because they are expensive catalytic systems and their frequent replacement will be costly. Therefore, commercial exploitation of ionic liquid catalysts during alkylation is impossible unless they are efficiently regenerated and recycled.

Various methods for removing conjunct polymers from acidic ionic liquid catalysts in order to regenerate the catalysts have been devised. For example, see U.S. Patent Application Publication 2007/0142213.

Once the ionic liquid catalyst has been regenerated, the catalyst is generally recycled to the main reaction. Unfortunately, ionic liquid catalysts are very sensitive to air and moisture. Unless the recycle system is totally dry and free of oxygen, the catalyst can be damaged. Thus, while methods have been devised to regenerate ionic liquid catalysts, a method for safely transporting/recycling the catalyst is still a great need in the industry

SUMMARY

Provided is a process for safely transporting or recycling an ionic liquid catalyst based on chloroaluminates. The process comprises mixing a secondary alcohol with an ionic liquid based on chloroaluminate and allowing a reaction to occur forming an aluminum chloride adduct precipitate. The precipitate is filtered and the secondary alcohol removed, leaving a solid salt. This solid salt is the ionic liquid catalyst absent aluminum chloride, for example, Nbutylpyridinium chloride. This salt is recycled to the reactor. $AlCl_3$ is added to the salt prior to introduction into the reactor to remake to ionic liquid catalyst, for example, Nbutylpyridinium heptachloroaluminate.

Among other factors, it has been found that transporting or recycling the ionic liquid salt is much easier and safer than transporting or recycling the ionic liquid catalyst. The salt is not as sensitive to air and moisture as the catalyst, and thus can be transported more easily. The present process of using a secondary alcohol to precipitate the aluminum chloride offers a fast and efficient method for removing the aluminum chloride and obtaining the ionic liquid salt for recycle or other transport.

DETAILED DESCRIPTION

The present process is for the safe and effective transport or recycle of an ionic liquid catalyst which is based on chloroaluminates. It has been found that by reacting an ionic liquid catalyst based on chloroaluminates with a secondary alcohol, the aluminum chloride in the catalyst forms a complex with the secondary alcohol.

This complex precipitates out of solution and can be removed by filtration. The remaining chloride salt of the ionic liquid catalyst in recovered by removing the secondary alcohol, e.g., by boiling off the alcohol, and leaving the chloride salt as a solid. The solid salt can then be transported to the reactor, where the addition of $AlCl_3$ to the salt can reform the catalyst prior to introduction into the reactor.

The ionic liquid catalyst can be any ionic liquid based upon chloroaluminates. One example of an ionic liquid catalyst is an amine-based cationic species mixed aluminum chloride like 1-alkyl-pyridinium chloroaluminate, such as 1-butyl-pyridinium heptachloroaluminate. Preferably the ionic liquid catalyst is selected from the group consisting of:

a chloroaluminate ionic liquid catalyst comprising a hydrocarbyl substituted pyridinium halide of the general formula A below and aluminum trichloride or a hydrocarbyl substituted imidazolium halide of the general formula B below and aluminum trichloride, preferably in 1 molar equivalent hydrocarbyl substituted pyridinium halide or hydrocarbyl substituted imidazolium halide of the general formulas A and B, respectively, to 2 molar equivalents aluminum trichloride;

a chloroaluminate ionic liquid catalyst comprising an alkyl substituted pyridinium halide of the general formula A below and aluminum trichloride or an alkyl substituted imidazolium halide of the general formula B below and aluminum trichloride, preferably in 1 molar equivalent alkyl substituted pyridinium halide or alkyl substituted imidazolium halide of the general formulas A and B, respectively, to 2 molar equivalents aluminum trichloride;

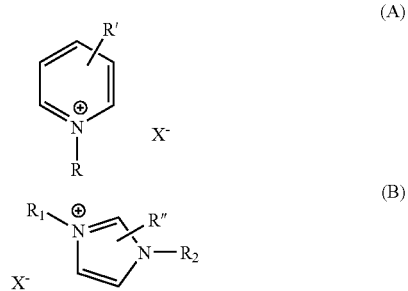

and mixtures thereof, where R=H, methyl, ethyl, propyl, butyl, pentyl, hexyl or benzyl, group R' and R"=H, methyl, ethyl, propyl, butyl, pentyl, hexyl, or benzyl group, and X is a haloaluminate, and preferably a chloroaluminate, and $R_1$ and $R_2$=H, methyl, ethyl, propyl, butyl, pentyl, hexyl or benzyl group, and where $R_1$ and $R_2$ may or may not be the same.

Another example of an ionic liquid catalyst is an alkyl substituted ammonium halide of the general formula C, mixed in with aluminum trichloride;

where R=H, methyl, ethyl, propyl, butyl, pentyl, hexyl, or benzyl group; $R_1$, $R_2$ and $R_3$=methyl, ethyl, propyl, butyl, pentyl, hexyl or benzyl group, X is a haloaluminate.

Ionic liquids containing $Al_2Cl_7$ or $AlCl_4$ can also be suitable. The present process can be used whenever such an ionic liquid based upon a chloroaluminate needs to be transported or recycled. Generally, the process finds particular application after an ionic liquid catalyst has been regenerated after being spent in a hydrocarbon conversion reaction. One such reaction is an alkylation reaction.

Various methods are known for regenerating spent ionic liquid catalysts. For example, see U.S. Patent Application Publication 2007/0142213, and U.S. Ser. Nos. 12/003,578 and 12/003,577, which are incorporated herein by reference in its entirety. These methods can remove conjoint polymers and provide a regenerated ionic liquid catalyst.

Once the catalyst has been regenerated, and the catalyst is ready for transport or recycle, the catalyst is mixed with a secondary alcohol. The secondary alcohol can be isopropanol, 2-butanol, 2-hexanol, 2-heptanol, or any suitable secondary alcohol which forms an adduct with $AlCl_3$, and which adduct has a solubility which allows it to form a precipitate. Isopropanol is preferred as the secondary alcohol, as it has been found to work most effectively in creating an adduct with the $AlCl_3$, which forms a precipitate. The isopropanol also allows easy removal to thereby recover the ionic liquid salt.

The formed precipitate is filtered and removed from the solution. The secondary alcohol is then removed, e.g., by boiling off/evaporation of the alcohol. Removal of the secondary alcohol leaves the chloride salt of the ionic liquid catalyst as a solid salt. Generally, the chloride salt of the ionic liquid catalyst is a solid salt. Generally, the chloride salt will also contain some $AlCl_3$ which did not form an adduct, or the adduct remains in solution. More than 90% of the $AlCl_3$ is generally separated out with the adduct, leaving no more than 10% in solution. The amount of $AlCl_3$ left in solution as dissolved adduct can be further reduced by cooling the solution. The lower the temperature, the more $AlCl_3$ adduct that will generally precepitate. The amount of $AlCl_3$ left in solution can be reduced to 6%, 5% or even less.

The solid chloride salt can then be transported to the reactor or a holding tank without issues concerning exposure to air, which would exist when recycling the ionic liquid catalyst itself. Once the salt is needed as catalyst, the addition of $AlCl_3$ to the salt will reform the catalyst prior to introduction into the reactor. The reformation can take place in a holding tank, reformation tank or just prior to introduction to the reactor.

The following example is provided to further illustrate the embodiments of the present process. It is meant to be only illustrative, and not limiting.

EXAMPLE 5 ml (about 6.7 gm) Nbutylpyridinium heptachloroaluminate was injected into 55 ml isopropanol at 50-60° C., and left stirring for 15 minutes. After 1 minute the solution turned opaque and some precipitate started to form. The mixture was then cooled to about 20° C. and a white precipitate filtered off. The solid was dried in nitrogen yielding 10.36 g white powder with an aluminum content of 7.65% corresponding to 0.80 g Al. The solution was concentrated to dryness yielding 3.27 g yellow crystalline solid containing 1.63% Al, corresponding to 0.05 g. Thus, 94% of the aluminum was removed with the white solid precipitate, leaving only 6% in the recovered salt, once the isopropanol is removed.

Precipitation at a lower temperature, e.g. 0° C. or lower, will generally result in an even better separation, and thus lower aluminum content in the recovered salt. Further lowering of the aluminum content may not be necessary, however, if the salt is simply to be recycled to the reaction process, where AlCl₃ is added to the salt in order to reform the ionic liquid catalyst.

Thus, the present process offers one a simple process for safely transporting the salt of an ionic liquid\d catalyst which can later be used to reform the catalyst. The process is simple enough to be performed on-site in the refinery. The white precipitate adduct is highly soluble in water and can be disposed of as an aqueous solution or exported as a chemical or for further chemical processing.

Although the present invention has been described in connection with preferred embodiments thereof, it will be appreciated by those skilled in the art that additions, deletions, modifications and substitutions not specifically described may be made without departing from the spirit and scope of the invention as defined in the appended claims.

That which is claimed is:

1. A process for preparing a salt of an ionic liquid based on a chloroaluminate comprising:
    mixing an ionic liquid based on a chloroaluminate with a secondary alcohol and forming an aluminum chloride adduct precipitate;
    removing the precipitate; and
    removing the secondary alcohol to thereby leave a halide salt of the ionic liquid.

2. A process according to claim 1, wherein the ionic liquid is selected from the group consisting of:
    a first chloroaluminate ionic liquid comprising a hydrocarbyl substituted pyridinium halide of the general formula A and aluminum trichloride or a hydrocarbyl substituted imidazolium halide of the general formula B and aluminum trichloride;
    a second chloroaluminate ionic liquid comprising an alkyl substituted pyridinium halide of the general formula A and aluminum trichloride or an alkyl substituted imidazolium halide of the general formula B and aluminum trichloride;
    and mixtures thereof,
wherein the general formula A and the general formula B are represented by the structures:

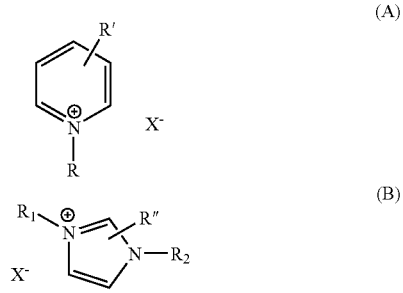

wherein R=H, methyl, ethyl, propyl, butyl, pentyl, hexyl or benzyl group, R' and R"=H, methyl, ethyl, propyl, butyl, pentyl, hexyl or benzyl group, and X is a haloaluminate, and R₁ and R₂=H, methyl, ethyl, propyl, butyl, pentyl, or hexyl or benzyl group and where R₁ and R₂ may or may not be the same.

3. A process according to claim 2, wherein the first chloroaluminate ionic liquid catalyst is prepared by combining 1 molar equivalent of the hydrocarbyl substituted pyridinium halide or the hydrocarbyl substituted imidazolium halide with 2 molar equivalents of aluminum trichloride.

4. A process according to claim 2, wherein the second chloroaluminate ionic liquid catalyst is prepared by combining 1 molar equivalent of the alkyl substituted pyridinium halide or the alkyl substituted imidazolium halide with 2 molar equivalents of aluminum trichloride.

5. A process according to claim 1, wherein the ionic liquid is an alkyl substituted ammonium halide of the general formula C, and aluminum trichloride,

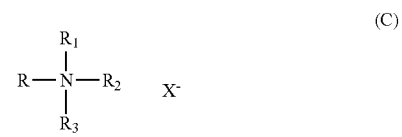

where R=H, methyl, ethyl, propyl, butyl, pentyl, hexyl, or benzyl group; R₁, R₂ and R₃=methyl, ethyl, propyl, butyl, pentyl, hexyl or benzyl group, and X is a haloaluminate.

6. A process according to claim 1, wherein the ionic liquid is N-butylpyridinium heptachloroaluminate.

7. A process according to claim 1, wherein the halide salt is N-butylpyridinuim chloride.

8. A process according to claim 1, wherein the mixing takes place at a temperature of room temperature or lower.

9. A process according to claim 8, wherein the mixing takes place at a temperature of 20° C. or less.

10. A process according to claim 1, wherein the secondary alcohol is isopropanol.

11. A process according to claim 1, wherein the ionic liquid is a catalyst.

12. A process according to claim 11, wherein the process further comprises recycling the halide salt to a reactor and adding AlCl₃ to the halide salt to remake the catalyst prior to introducing into the reactor.

13. A process according to claim 12, wherein the reactor is an alkylation reactor.

14. A method of transporting an ionic liquid based on a chloroaluminate comprising:
    mixing an ionic liquid based on a chloroaluminate with a secondary alcohol and forming an aluminum chloride adduct precipitate;
    removing the precipitate,
    removing the secondary alcohol to thereby leave a halide salt of the ionic liquid, and transporting the halide salt to a selected destination.

15. A method according to claim 1, further comprising adding aluminium trichloride to the halide salt at the destination to reform the ionic liquid.

16. A method according to claim 15, wherein the destination is an alkylation reactor and the ionic liquid is reformed prior to introduction into in the reactor.

17. A method according to claim 14, wherein the ionic liquid is selected from the group consisting of:
    a first chloroaluminate ionic liquid comprising a hydrocarbyl substituted pyridinium halide of the general formula A and aluminum trichloride or a hydrocarbyl substituted imidazolium halide of the general formula B and aluminum trichloride;
    a second chloroaluminate ionic liquid comprising an alkyl substituted pyridinium halide of the general formula A and aluminum trichloride or an alkyl substituted imidazolium halide of the general formula B and aluminum trichloride;

and mixtures thereof, wherein the general formula A and the general formula B are represented by the structures:

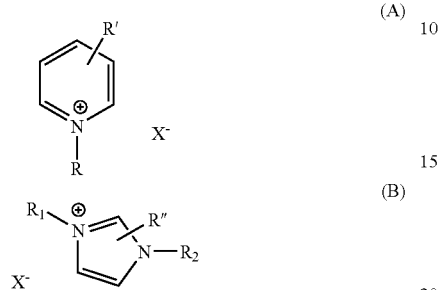

(A)

(B)

wherein R=H, methyl, ethyl, propyl, butyl, pentyl, hexyl or benzyl group, R' and R"=H, methyl, ethyl, propyl, butyl, pentyl, hexyl or benzyl group, and X is a haloaluminate, and $R_1$ and $R_2$=H, methyl, ethyl, propyl, butyl, pentyl, hexyl or benzyl group and where $R_1$ and $R_2$ may or may not be the same.

18. A method according to claim 17, wherein the first chloroaluminate ionic liquid catalyst is prepared by combining 1 molar equivalent of the hydrocarbyl substituted pyridinium halide or the hydrocarbyl substituted imidazolium halide with 2 molar equivalents of aluminum trichloride.

19. A method according to claim 17, wherein the second chloroaluminate ionic liquid catalyst is prepared by combining 1 molar equivalent of the alkyl substituted pyridinium halide or the alkyl substituted imidazolium halide with 2 molar equivalents of aluminum trichloride.

20. A method according to claim 14, wherein the ionic liquid is an alkyl substituted ammonium halide of the general formula C, and aluminum trichloride,

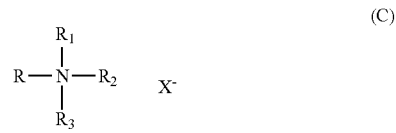

(C)

where R=H, methyl, ethyl, propyl, butyl, pentyl, hexyl, or benzyl group; $R_1$, $R_2$ and $R_3$ =methyl, ethyl, propyl, butyl, pentyl, hexyl or benzyl group, and X is a haloaluminate.

21. A method according to claim 14, wherein the ionic liquid is N-butylpyridinium heptachloroaluminate.

22. A method according to claim 14, wherein the halide salt is N-butylpyridinium chloride.

23. A method according to claim 14, wherein the mixing takes place at a temperature of room temperature or lower.

24. A method according to claim 23, wherein the mixing takes place at a temperature of 20° C. or less.

25. A method according to claim 14, wherein the secondary alcohol is isopropanol.

26. A method according to claim 14, wherein the ionic liquid is a catalyst.

* * * * *